United States Patent [19]

Gotfried

[11] Patent Number: 5,690,640
[45] Date of Patent: Nov. 25, 1997

[54] SURGICAL INSTRUMENT FOR USE DURING CONNECTION OF FRACTURED BONES

[76] Inventor: Yehiel Gotfried, 10, Ben Gurion Avenue, Kiryat Bialik 27000, Israel

[21] Appl. No.: 371,300

[22] Filed: Jan. 11, 1995

[30] Foreign Application Priority Data

Jun. 8, 1994 [IL] Israel .................................. 109929

[51] Int. Cl.$^6$ ................................................ A61B 17/56
[52] U.S. Cl. .......................... 6066/105; 606/86; 606/72
[58] Field of Search ................................ 606/105, 105.5, 606/101, 88, 87, 86, 96, 69, 70, 71, 205, 206, 207, 208

[56] References Cited

U.S. PATENT DOCUMENTS

| | | | |
|---|---|---|---|
| 2,631,585 | 3/1953 | Siebrandt | 606/208 |
| 3,604,414 | 9/1971 | Borges | 606/105 |
| 3,828,791 | 8/1974 | Santos | 606/207 |
| 5,133,724 | 7/1992 | Wilson, Jr. et al. | 606/151 |

FOREIGN PATENT DOCUMENTS 1169404  12/1958  France .................................. 606/105

*Primary Examiner*—Guy V. Tucker
*Attorney, Agent, or Firm*—Frishauf, Holtz, Goodman, Langer & Chick

[57] ABSTRACT

A surgical device for clamping a connector plate onto a fractured bone is configured to be inserted into the limb through a small incision in the skin and the tissue. It includes a first member in the form of a hook for gripping the rear surface of the bone and for cutting through muscle and tissue by means of a knife blade forming the back of the hook, and of a screw-threaded bar and handle which extend to the outside of the limb. A second member includes a tube slidingly movable on the bar of the first member, which has its inner end shaped to form a hook for gripping the connector plate. The two hooks are pulled together by a winged nut screwed onto the bar, thereby pressing the plate onto the bone. The hook of the second member may be pivotally attached to it so as to readily fit onto the plate contour.

8 Claims, 6 Drawing Sheets

SURGICAL INSTRUMENT FOR USE DURING CONNECTION OF FRACTURED BONES

The invention relates to a surgical instrument to be used during connection of two fractured bone portions by means of a connector plate screwed to the fractured parts. It relates particularly to an instrument suitable for pressing this connector plate onto the bone surface during percutaneous surgery while drilling holes for subsequent insertion of connection screws.

BACKGROUND OF THE INVENTION

Connection of fractured bone parts is either performed by insertion of an intramedullary nail configured to draw the parts together, by an external fixation device, or by a plate attached to the fractured bone portions and fastened by long screws passing through the solid bone material. A special case is the re-connection of a fractured femur head which is usually performed by the insertion of one or two long screws or bolts through the trochanter area into the head while these screws are attached to a connector plate which, in its turn, is connected to the femur shaft by two or more screws. It is an important task to keep the plate in proper alignment and clamped to the bone material during drilling the bone for insertion of the screws. It is a particularly difficult task to keep the connector plate in position while using the surgical instrument disclosed by the present inventor in Israeli Patent No. 105,183. This instrument includes a connector plate which is inserted into the tissue percutaneously through a small incision in the skin and is slid along the bone into its proper position by means of a special connector arm. However, even if the connector arm is firmly held, there is always the possibilty that the connector plate moves from its designated place on the bone while holes are drilled for subsequent insertion of screws, particularly because the plate is not directly visible having been inserted percutaneously. The same occurrence is apt to happen in the case of an operation of any other kind of fracture with the aid of a differently shaped connector plate, used in a percutaneous operation.

There exist a number of surgical instruments designed for clamping the connector plate in position while pressing it onto the fractured bone; however, all these are relatively volumenous and clumsy and are not suitable for insertion into the limb through a relatively small incision through skin and tissue, as required during a percutaneous operation. The conventional instruments are not suitable for dissection through soft tissue in order to reach the bone proper.

It is, therefore, the main object of the invention to provide a tool or instrument suitable for percutaneous insertion through a relatively small incision through the skin and the soft tissue and for holding any kind of connector plate in position and to clamp it to the fractured bone parts.

And it is another object to provide an instrument which is easy to handle, which is of simple construction and can be readily sterilized.

SUMMARY OF THE INEVNTION

In the present description of the invention the expression "near" will be used to define the portion of the fractured bone facing the incision in the skin, while the expression "far" will be used for the opposite side.

A preferred embodiment of the surgical instrument configured to be inserted percutaneously and to hold a connector plate in position on a fractured bone while pressing it onto the bone surface essentially inludes the following components:

a first hook-shaped member serving to grip the far side of the bone, wherein one end of the hook is continued in the form of a long straight screw-threaded bar extending to the outside of the limb while the back of the hook is narrowed to form a sharp chisel or knife blade, a second hook-shaped member serving to grip a connector plate placed onto the near side of the bone with one end of the hook-shaped member continued in the form of a tube slidingly movable along the straight bar and terminating at its outer end in the form of a grip, a straight handle releasably attachable onto the outer end of the threaded bar, and a winged nut movable on the threaded bar.

In a first embodiment the hook-shaped members are provided with toothed surfaces facing the bone, while in another embodiment these surfaces are shaped to safely enclose a connector plate.

In another embodiment the second member includes a toothed hook pivotally attached to a lug extending sideways from the tube, enabling the hook to engage a connector plate which is positioned in angular alignment on the bone.

In a third embodiment the inside of the hooks is smooth and shaped in the form of a connector plate to be clamped.

The instrument is inserted into the limb through a small cut in the skin and tissue made parallel to the direction of the bone and is pushed into the limb while cutting through soft tissue and muscles, until the two hooks are positioned to one side of the bone, with the hook of the first member on the far side and that of the second member on the near side. Now the first member is gradually turned about a right angle with the sharp edge pushing through muscle and tissue until the hook grips the rear side of the bone. Thereafter the second member is similarly turned until its teeth face the connector plate. The second member is urged towards the plate by rotation of the winged nut, until the plate is firmly pressed onto the bone and held there. After drilling the bone material through the holes in the connector plate and fastening the screws through the plate or plates and the bone, the instrument is removed in the reverse order, permitting the wound to be sutured and dressed.

DETAILED DESCRIPTION OF THE DRAWINGS

Figure 1:
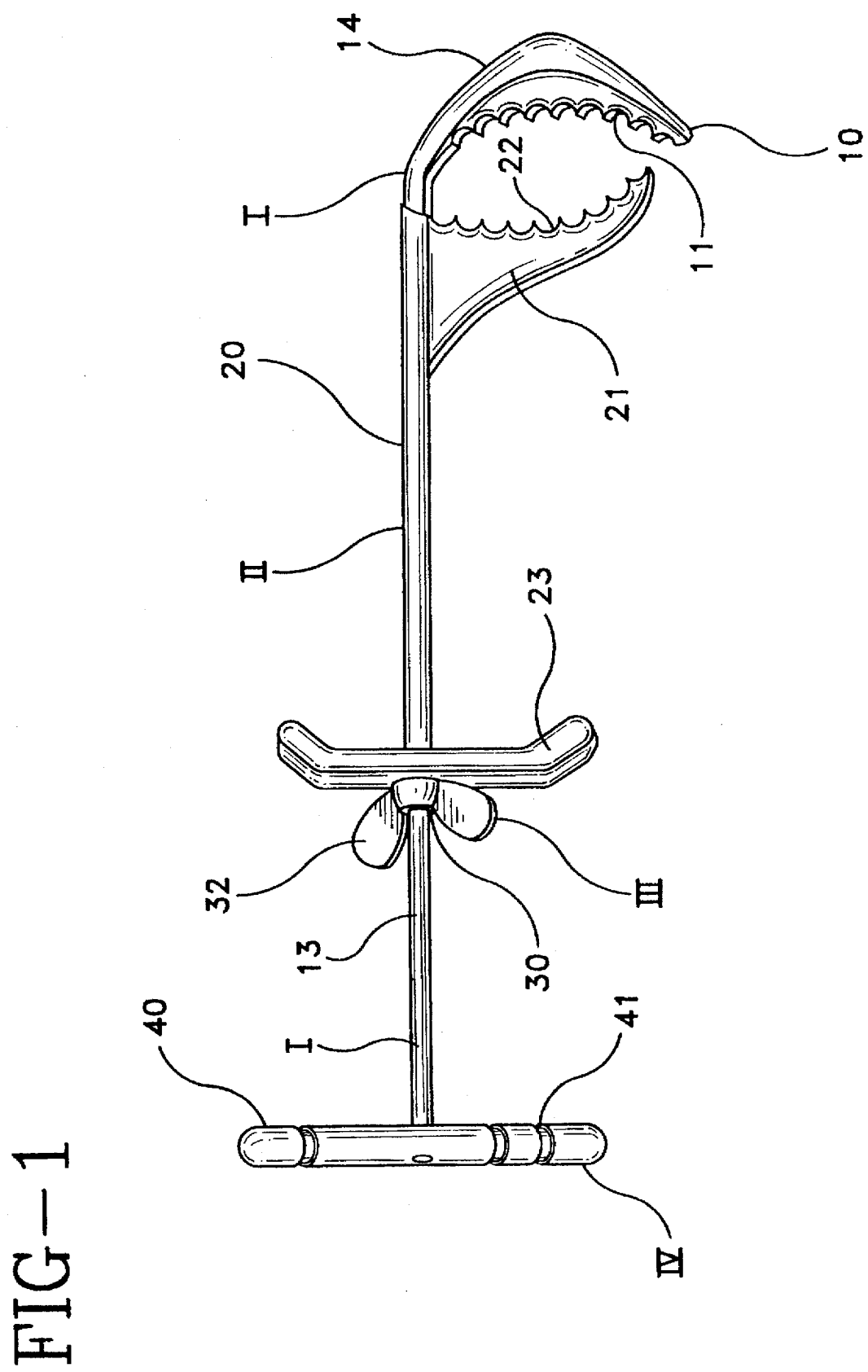
FIG. 1 shows a preferred embodiment of the surgical instrument according to the invention, in fully assembled state, illustrating the connection of a handle to the straight bar of the first member
Figure 2:
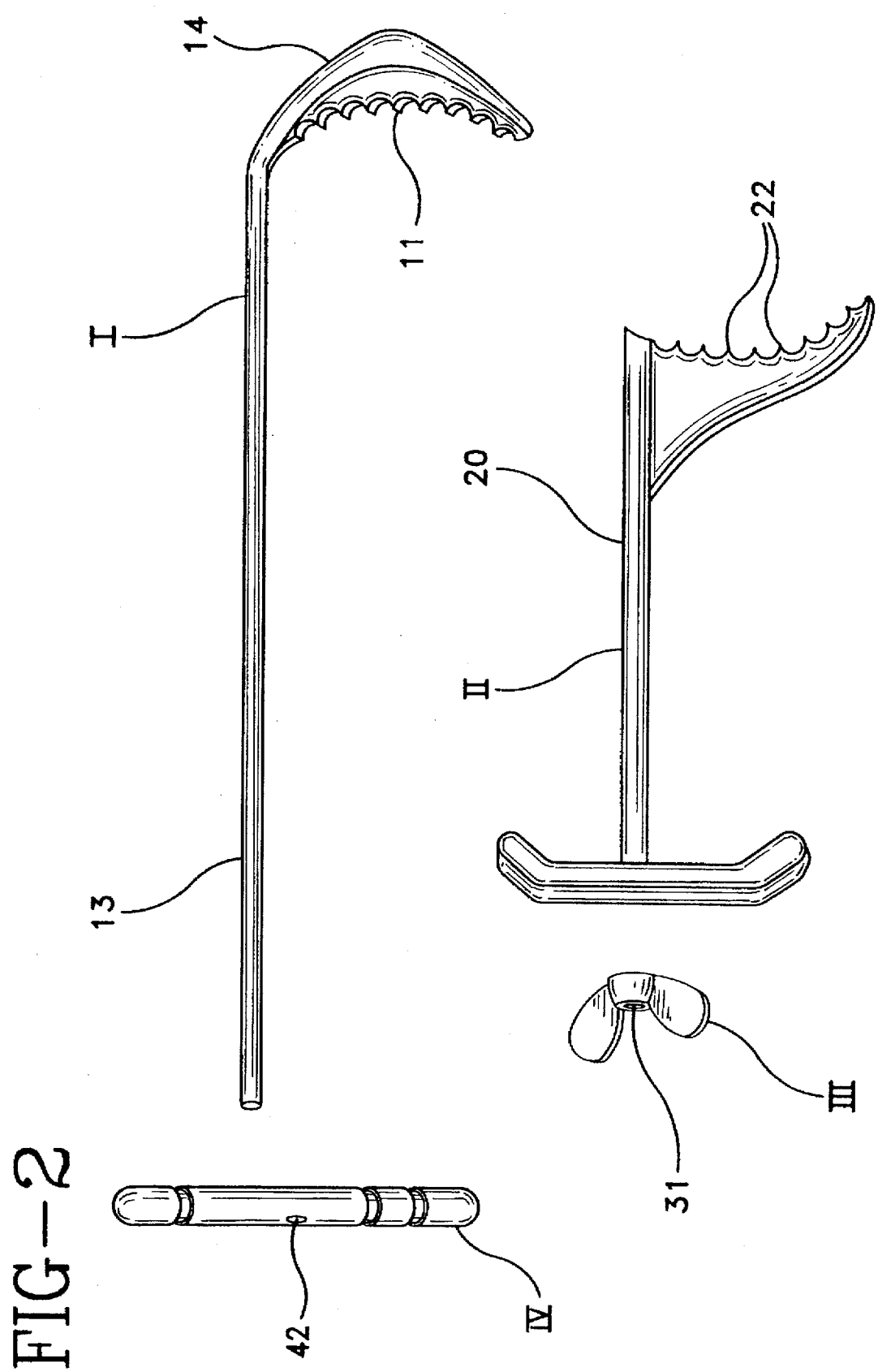
FIG. 2 shows the different components of the instrument of FIG. 1 in disassembled state.

The instrument illustrated in FIGS. 1 and 2 includes a first hook-shaped member I, a second hook-shaped member II, a winged nut III and a straight handle IV. The first member is composed of a rounded hook 10 having a toothed inside surface 11, with one end of the hook continued in the shape of a screw-threaded straight bar 13 which, during an operation extends to the outside of the limb towards the surgeon. The back or outer surface 14 of the hook is narrowed to form a sharp chisel or knife blade configured to cut its way through muscle and tissue.

The second member is composed of a tube 20 which is slipped over bar 13 and is slidingly movable along this bar, the tube ending in a hook 21 open towards the hook of the first member and has the side opposite the first hook provided with teeth 22. The other end of the tube forms a grip 23 permitting ready positioning and adjustment of the instrument on the bone and on the connector plate. The third component is a winged nut III composed of a central hub 30 perforated by femal screw thread 31 cooperating with the thread on bar 13 and of two opposed wings 32. The handle IV is in the form of a straight bar 40 suitably grooved (41) to provide for a firm grip and is centrally perforated by a screw-threaded bore 42, the screw-thread cooperating with that of bar 13.

Figure 3:
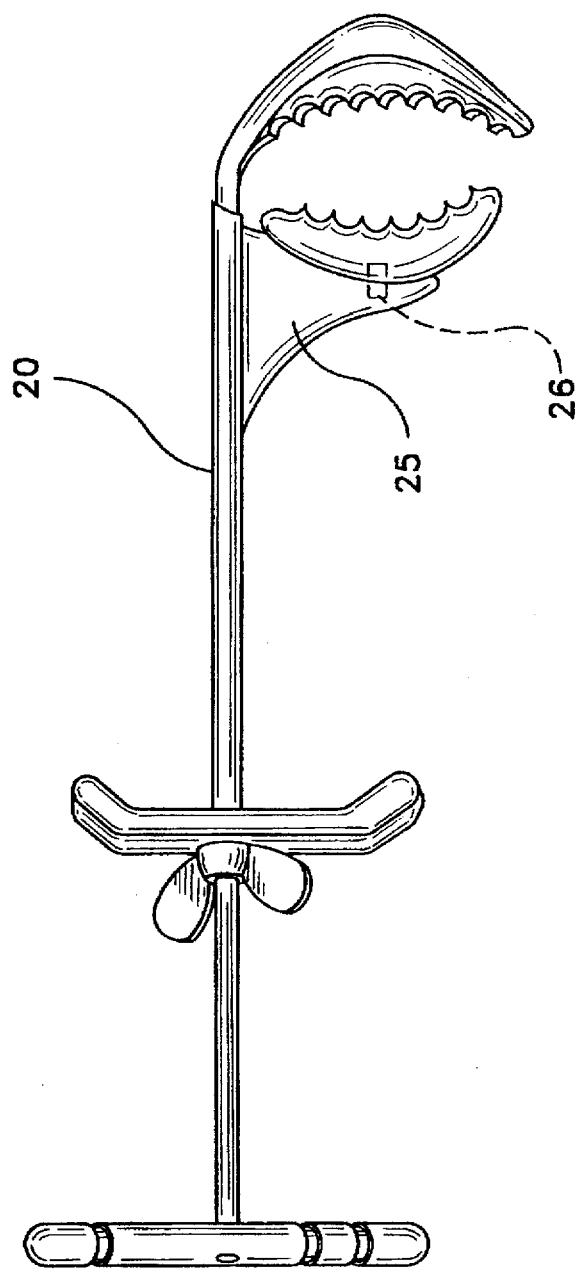
FIG. 3 illustrates the instrument of FIG. 1 with the addition of the hook of the second member pivotally attached to this member.

The instrument shown in FIG. 3 is substantially identical with that illustrated in FIG. 1, except for the hook of the second member which is pivotally attached to a lug 25 at the far end of the tube 20 by means of a pin 26. All remaining parts are identical with those of the instrument of FIG. 1.

Figure 4:
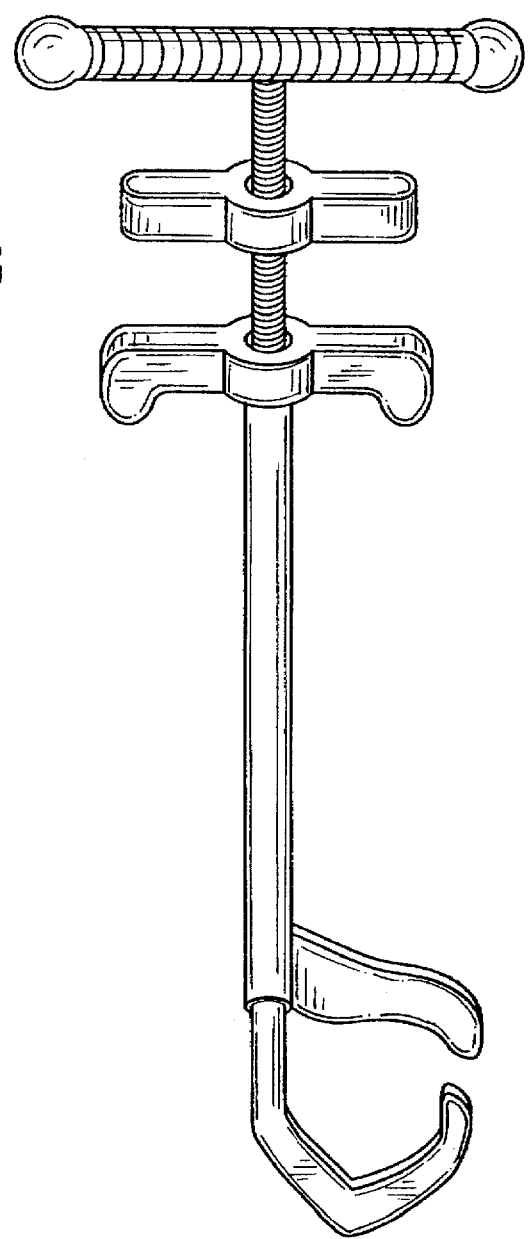
FIG. 4 shows a slightly modified embodiment of the instrument shown in FIG. 1.

The instrument of FIG. 4 is substantially identical with that of FIGS. 1 and 2, with the difference that the inside of the hooks is not toothed, but shaped in the form of a connector plate which it is intended to clamp onto the bone.

Figure 5:
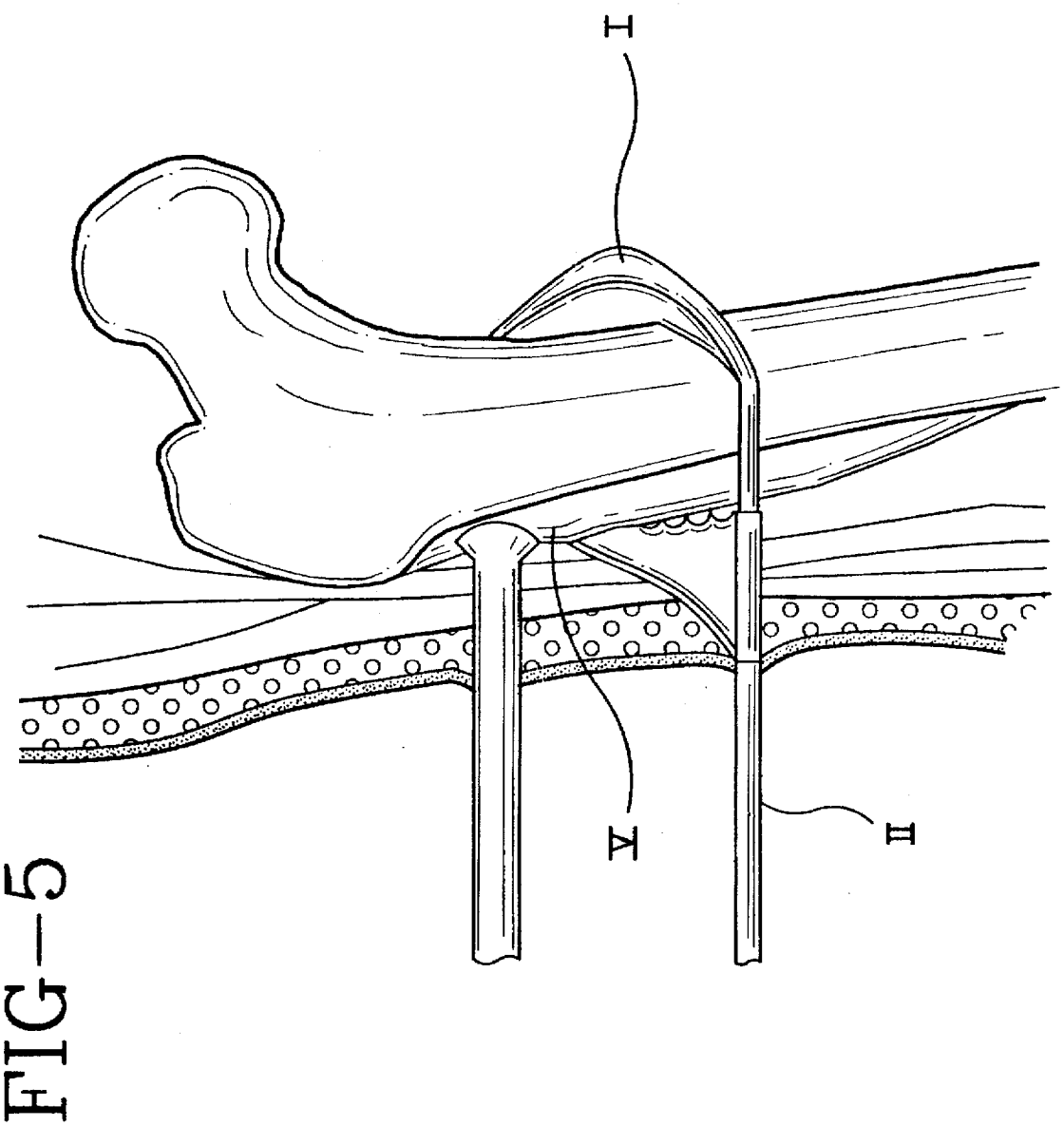
FIG. 5 shows the instrument clamping a connector plate onto the femur shaft of a fractured femur neck.
Figure 6:
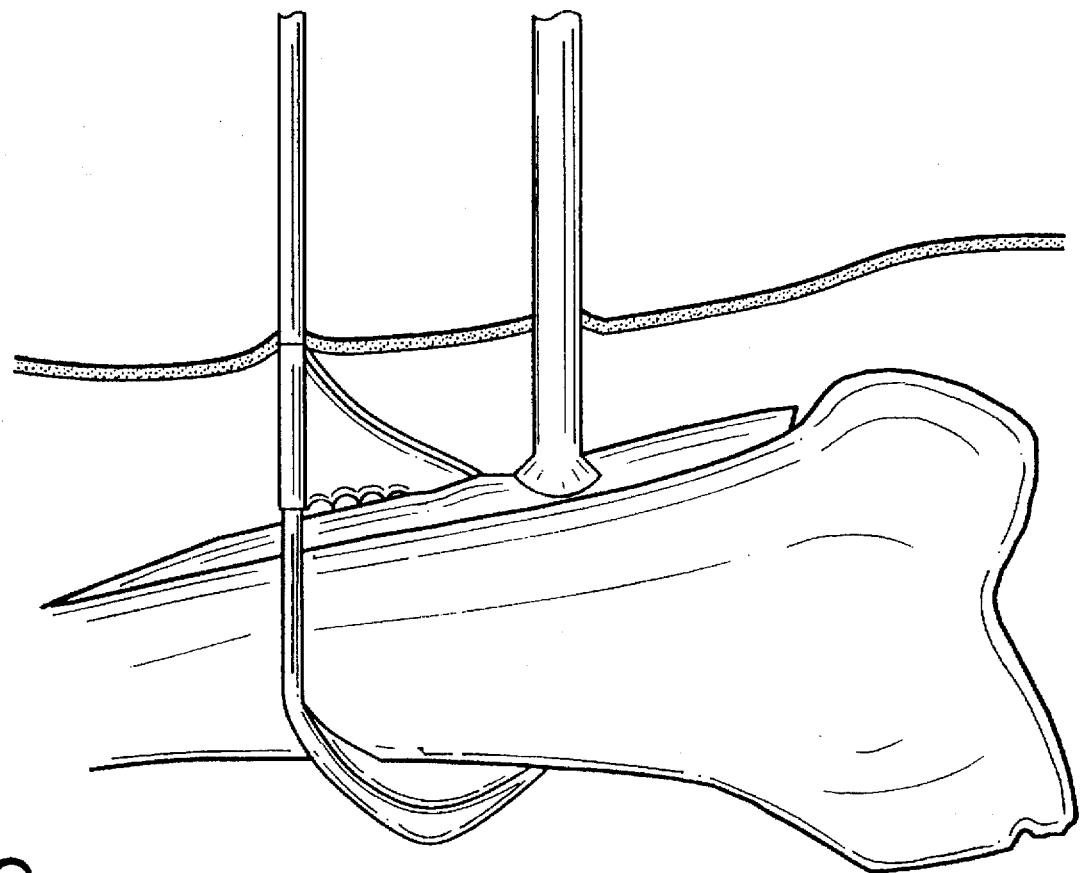
FIG. 6 shows the instrument clamping a connector plate onto the two portions of a fractured bone.
Figure 7:
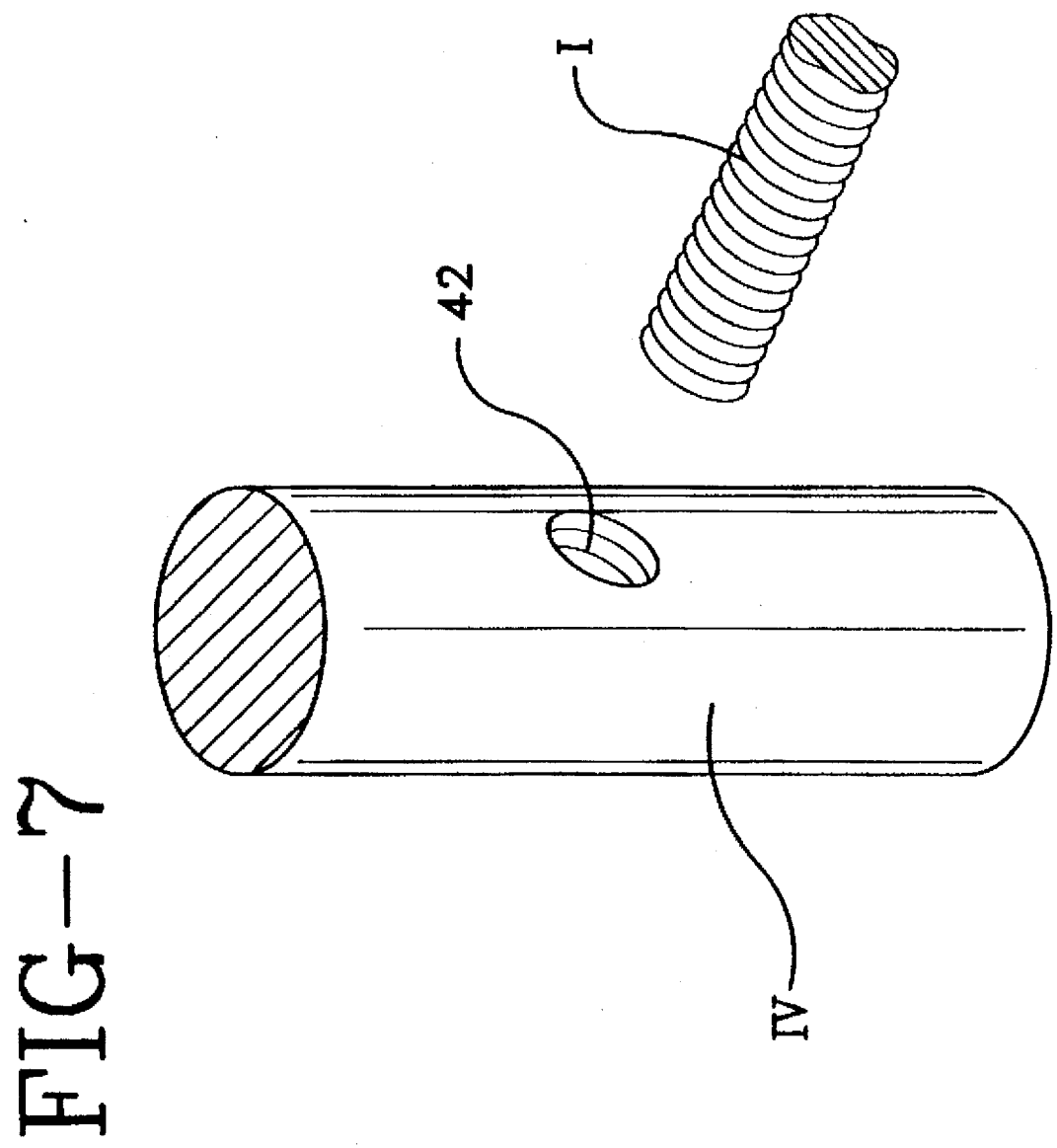
FIG. 7 is a perspective view of the central tapped bore in the handle for mounting the handle on the straight bar.

As described hereinbefore, the instrument is pushed into the limb through a small incision in the skin, cutting its way through soft tissue and muscle, until it lies parallel to the bone. The first member is now turned about a right angle with the aid of handle IV until it grips the rear side of the bone, as visible in FIGS. 5 and 6. Now the other hook is turned about a right angle until it faces the connector plate V and is urged towards the latter by means of the winged nut III, until the plate is firmly clamped onto the bone, permitting safe drilling and inserting of screws.

It will be understood that the shape of the different components of the instrument as appearing in the accompanying drawings may be slightly changed to suit various kinds of needs and modes of manufacture, provided the first hook-shaped member has a chisel- or knife-shaped back.

It is, for instance proposed to fasten handle IV to bar 13 of the first member by means of a square hole mounted on the correspondingly sized end of the bar. Urging of the second member onto the connector plate may be carried out by other means as that shown in the drawings as, for instance, by pawl and ratchet action.

I claim:

1. A surgical instrument adapted to cooperate with a part of a human body so as to be used for percutaneous insertion into a limb through a small incision and for holding a connector plate in a correct position on a fractured bone while pressing the connector plate onto a surface of the bone, the instrument having a proximal end and a distal end, and the instrument comprising:

a first member including:

a distal end, a first hook at the distal end of the first member, the first hook having a concave surface pointing towards the proximal end of said instrument, and said first hook having a distal side which is shaped to form a chisel/knife blade for cutting through tissue and muscle, and a straight bar extending from one end of said first hook and extending in a proximal direction toward the proximal end of the instrument, and said bar having a proximal end, a second member including:

a distal end, a second hook at the distal end of the second member, the second hook having a concave surface pointing towards the distal end of said instrument, and a tube extending from one end of said second hook and extending in said proximal direction, said tube slidably arranged on said straight bar of said first member, and said tube having a proximal end and a distal end, a first handle provided at the proximal end of said straight bar of said first member for turning said straight bar, a device for moving said tube of said second member along said bar of said first member and for urging said second hook of said second member towards said bone and onto said connector plate in order to hold said connector plate in its correct position on the fractured bone.

2. The surgical instrument of claim 1, wherein the concave surfaces of said hooks of both said first member and said second member are provided with teeth.

3. The surgical instrument of claim 1, wherein:

the concave surface of said first hook of said first member is a toothed concave surface for gripping the bone, and the concave surface of the second hook of said second member is shaped to conform to said connector plate.

4. The surgical instrument of claim 1, wherein the concave surfaces of said hooks of both said first member and said second member are smooth.

5. The surgical instrument of claim 1, wherein said second member includes a lug extending sideways from the distal end of said tube of said second member, and the second hook is pivotally attached to said lug.

6. The surgical instrument of claim 1, wherein said straight bar of said first member is screw-threaded and includes a winged nut mounted close to the proximal end of said tube of said second member for rotation on said bar in order to urge said second hook of said second member onto said connector plate.

7. The surgical instrument of claim 6, wherein said first handle at the proximal end of said straight bar of said first member includes a central tapped bore for mounting said handle on the proximal end of said screw-threaded bar.

8. The surgical instrument of claim 1, wherein the device for moving and urging includes a second handle fixedly attached to the proximal end of said tube of said second member.

* * * * *